(12) United States Patent
Levinson et al.

(10) Patent No.: US 6,926,695 B2
(45) Date of Patent: Aug. 9, 2005

(54) SEALANT APPLICATOR AND METHOD EMPLOYING IMPULSE CLEARING

(75) Inventors: Mitchell E. Levinson, Pleasanton, CA (US); Gordon Howard Epstein, Fremont, CA (US)

(73) Assignee: Baxter International Inc., Deerfield, IL (US)

(*) Notice: Subject to any disclaimer, the term of this patent is extended or adjusted under 35 U.S.C. 154(b) by 133 days.

(21) Appl. No.: 10/377,248

(22) Filed: Feb. 27, 2003

(65) Prior Publication Data

US 2003/0229305 A1 Dec. 11, 2003

(51) Int. Cl.$^7$ ............................. A61M 5/00; B67D 5/60
(52) U.S. Cl. ..................... 604/191; 604/214; 604/218; 222/145.2
(58) Field of Search ........................... 604/191, 82, 83, 604/89, 218; 606/213, 214; 222/145.2, 145.5, 145.6, 631, 135, 136

(56) References Cited

U.S. PATENT DOCUMENTS

| | | | |
|---|---|---|---|
| 2,812,765 A | 11/1957 | Tofflemire | |
| 3,065,749 A | 11/1962 | Brass | |
| 3,159,312 A | 12/1964 | Van Sciver, II | |
| 3,188,056 A | 6/1965 | Trumbull et al. | |
| 3,556,346 A | 1/1971 | Brislow | |
| 3,828,980 A | 8/1974 | Creighton et al. | |
| 4,040,420 A | 8/1977 | Speer | |
| 4,067,479 A | 1/1978 | Moline | |
| 4,109,653 A | 8/1978 | Kozam et al. | |
| 4,325,913 A | 4/1982 | Wardlaw | |
| 4,359,049 A | 11/1982 | Redl et al. | |
| 4,471,887 A | 9/1984 | Decker | |
| 4,631,055 A | 12/1986 | Redl et al. | |
| 4,688,702 A | * 8/1987 | Yeames | ................... 222/145.2 |
| 4,735,616 A | 4/1988 | Eibl et al. | |

(Continued)

FOREIGN PATENT DOCUMENTS

| | | |
|---|---|---|
| EP | 0037393 | 6/1983 |
| EP | 0156098 | 11/1989 |
| WO | WO 96/39212 | 12/1996 |

OTHER PUBLICATIONS

U.S. Appl. No. 09/302,726, Epstein, filed Apr. 1999.

*Primary Examiner*—Sharon Kennedy
(74) *Attorney, Agent, or Firm*—Jeffrey C. Nichols

(57) ABSTRACT

A sealant applicator suitable for dispensing a coagulable sealant, for example a two-component fibrin sealant mixed in the applicator, employs impulse clearing to remove residual coagulated or coagulating material from the dispensing pathway and mixing chamber, if present. Impulses may be generated by manual application of a clearing member such as a plunger which can enter into the dispensing pathway to engage, dislodge and discharge residuals or can generate a gas impulse to impact the residuals to similar effect. A clearing valve having a clearing port can be operated by movement of the clearing member to provide access to the dispensing pathway.

14 Claims, 2 Drawing Sheets

U.S. PATENT DOCUMENTS

| | | |
|---|---|---|
| 4,776,840 A | 10/1988 | Freitas et al. |
| 4,874,368 A | 10/1989 | Miller et al. |
| 4,978,336 A | 12/1990 | Capozzi et al. |
| 5,116,315 A | 5/1992 | Capozzi et al. |
| 5,226,877 A | 7/1993 | Epstein |
| 5,299,740 A | 4/1994 | Bert |
| 5,304,165 A | 4/1994 | Haber et al. |
| 5,328,459 A | 7/1994 | Laghi |
| 5,395,326 A | 3/1995 | Haber et al. |
| 5,405,607 A | 4/1995 | Epstein |
| 5,447,494 A | 9/1995 | Dorsey, III |
| 5,474,540 A | 12/1995 | Miller et al. |
| 5,520,658 A | 5/1996 | Holm |
| 5,585,007 A | 12/1996 | Antanavich et al. |
| 5,605,255 A | 2/1997 | Reidel et al. |
| 5,643,206 A | 7/1997 | Fischer |
| 5,648,265 A | 7/1997 | Epstein |
| 5,665,067 A | 9/1997 | Linder et al. |
| 5,887,755 A | 3/1999 | Hood, III |
| 5,971,956 A | 10/1999 | Epstein |
| 5,989,215 A | 11/1999 | Delmotte et al. |
| 6,007,515 A | 12/1999 | Epstein et al. |
| 6,047,861 A | 4/2000 | Vidal et al. |
| 6,063,055 A | 5/2000 | Epstein et al. |
| 6,113,571 A | 9/2000 | Zinger et al. |
| 6,331,172 B1 | 12/2001 | Epstein et al. |
| 6,733,472 B1 * | 5/2004 | Epstein et al. ............... 604/30 |

* cited by examiner

SEALANT APPLICATOR AND METHOD EMPLOYING IMPULSE CLEARING

CROSS-REFERENCE TO RELATED APPLICATIONS

The present application claims priority from U.S. patent application Ser. No. 09/315,702, filed on May 20, 1999, now U.S. Pat. No. 6,575,940, which claims the benefit of priority from U.S. provisional utility patent application Ser. No. 60/086,208 filed on May 21, 1998. This application discloses subject matter related to copending U.S. patent application Ser. Nos. 08/838,078 and 08/839,614, both filed Apr. 15, 1997, to patent application Ser. No. 08/946,364 filed Oct. 7, 1997, to patent application Ser. No. 09/037,160 filed Mar. 9, 1998 and to patent application Ser. No. 09/302,726 filed Apr. 30, 1999 all naming Gordon H. Epstein as first inventor. The disclosures of the aforementioned United States Patent applications, collectively referenced "the related applications" are hereby incorporated herein by reference thereto.

STATEMENT REGARDING FEDERALLY SPONSORED RESEARCH OR DEVELOPMENT (Not applicable.)

BACKGROUND OF THE INVENTION

1. Field of the Invention

The present invention relates to an applicator and method of applying fluid sealant agents to a work surface and is particularly, although not exclusively, useful for applying two-component tissue sealant agents to biological tissue to effect hemostasis or achieve other therapeutic results. More particularly, it relates to a hand-held applicator and methods of application of tissue sealants from a hand-held applicator.

2. Description of Related Art Including Information Disclosed under 37 CFR 1.97 and 37 CFR 1.98

Application of tissue sealants and other biologically derived or biologically functional materials to close wounds, control bleeding, control fluid leakage or oozing or to fulfill other therapeutic or preparative purposes, is an important emerging surgical technique, well adapted for the operating room or field environments such as the doctor's office or mobile medical units. Preferred sealants include fibrin sealants which are formed from blood plasma components and comprise, on the one hand, a first agent containing fibrinogen and Factor XIII, and on the other hand a second agent which usually includes thrombin, and calcium ions. The fibrinogen is capable of a polymerizing and being cross-linked to form a solid fibrin clot when the agents are mixed. The necessary additional factors to simulate relevant portions of the natural blood coagulation cascade are suitably distributed between the fibrinogen and thrombin agents.

High levels of protection against transmission of infections or induction of immunological reactions can be assured by using an autologous or single-donor source for both agents. Such sealants are highly effective, are biologically degraded without residue and may promote wound healing. Other biologically derived or biologically functional agents may be applied together with or in lieu of the tissue sealant.

Depending upon the potency of the particular formulations employed, polymerization or coagulation of the sealant may take place very rapidly, yielding a gel within perhaps 10 or 20 seconds. Though often desirable for surgical reasons, such fast-acting properties present potential problems of fouling or clogging. These problems must be overcome in devising suitable applicators, and methods of application.

Antanavich et al. U.S. Pat. No. 5,585,007, whose disclosure and references are hereby incorporated herein by reference thereto, provides an extensive discussion of the literature relating to fibrinogen sealant preparation (column 1, line 20 to column 4, line 62) and applicators column 4 line 62 to column 5, line 14), as well as a bibliography, (columns 6–10) and is a helpful guide to the teachings of prior workers in the field.

A popular manually operable applicator for such two-agent sealants employs a dual syringe construction having two syringes each of which provides a reservoir for one of the agents. Plungers, connected together by a yoke, are advanced within the syringes, to dispel the agents from the applicator. In many prior devices the sealant agents are discharged in separate streams and mixed externally of the applicator. Such applicators are similar in principle to household epoxy glue applicators commonly available in hardware stores, see for example Creighton et al. U.S. Pat. No. 3,828,980. Achieving effective mixing externally of the applicator is problematic and the resultant sealant product is often inadequately mixed and performs unsatisfactorily. Poor mixing may result in any one or more of the drawbacks of Slow polymerization, poor adhesion and cohesion, low bond strength, uneven distribution of the sealant on the work surface, inadequate coverage and poor film or spray formation.

It would be desirable to have a manually operable tissue sealant applicator which mixed two or more agents prior to discharge from the applicator, and in U.S. Pat. No. 5,266,877, and the above applications, Gordon H. Epstein, and others, teach various constructions of a dual syringe applicator which provide internal mixing. A problem that arises is that such an applicator must necessarily have a mixed agent pathway within the device, extending from a point of mixing of the agents to a point of discharge from the device, and this mixed agent pathway is prone to clogging, obstruction or contamination with gelled or solidified sealant.

In the related applications, the possibility of retrograde clearing of the mixed fluids pathway within the applicator, using suction, is also disclosed. Thus, the related applications teach a method of applying a tissue sealant or the like, which comprises mixing two or more sealant agents in an applicator, dispelling the mixed agents from the applicator along a mixed agent pathway and clearing the mixed agent pathway of undesired residues. In a preferred embodiment (of the related applications) the applicator is provided with suitable suction conduits and valving to apply suction to the work surface for various purposes, for example to prepare the work surface for the application of sealant, for example by removing fluids, or to grip and manipulate tissue. As taught, the valving is operable to effect retrograde clearing of a sealant dispensing pathway. Enhanced mixing results and problems of fouling by deposited solids are avoided. Drawbacks are that such applicators require a suitable suction source, which may not always be available, and the magnitude of the clearing force that can be applied by suction is limited.

Related application Ser. No. 09/037,160, also discloses an alternative embodiment of the above-described clearing method which comprises disposing of the clogged structures between sealant applications by removing a disposable agent from the applicator. For this purpose the applicator is provided with a disposable sealant dispensing cannula which may extend into a mixing chamber where the sealant agents are mixed. However, component disposability entails costs and inconveniences and may result in loss of valuable sealant of limited availability. Fast acting fibrinogen sealants that clot rapidly may require the cannula to be changed after every use, which may not be practical during a complex surgical procedure, It would therefore be desirable to have a sealant applicator and application method providing internal mixing which solves the prior art clogging problems without requiring a suction source or disposable components.

BRIEF SUMMARY OF THE INVENTION

The present invention solves these and other problems by providing, in one aspect, a manually operable sealant applicator capable of dispensing a sealant mixture comprising at least two sealant agents, the applicator having:

a) at least two supply pathways for respectively supplying at least two individual sealant agents;

b) a dispensing pathway for dispensing a mixture of the individual sealant agents, the dispensing pathway communicating with the supply pathways to receive the at least two sealant agents therefrom; and c) a manually actuatable clearing member to move undesired materials along the dispensing pathway.

In another aspect, the invention provides a manually operable sealant applicator capable of dispensing a coagulable sealant, the applicator having:

a) a variable volume reservoir for the sealant, the sealant being dischargeable from the reservoir by manually effected volume reductions;

b) a dispensing pathway for dispensing the sealant, the dispensing pathway communicating with the reservoir to receive the sealant therefrom;

c) a clearing valve communicating with the dispensing pathway and being movable between a dispensing position and a clearing position, the clearing valve providing access to the dispensing pathway in the clearing position; and d) a manually actuatable clearing member operable through the access provided by the clearing valve to move undesired materials along the dispensing pathway.

The invention also provides, in a further aspect, a method of dispensing a sealant comprising:

a) mixing two or more sealant agents in an applicator;

b) discharging the mixed agents from the applicator along a dispensing pathway; and c) applying an impulsive force to the dispensing pathway to clear the dispensing pathway of residual materials.

Preferably, the plunger is mechanically coupled to the applicator and is manually driven, for example by a resiliently biased control button or is pneumatically, or possibly even hydraulically, driven. If desired, a wiper, such as a doctor blade, can be provided to clean the distal head of the plunger of any adhering sealant, when retracted. Alternatively, a plunger drive mechanism can be constructed to expose the plunger head distally out of the dispensing pathway, for cleaning.

In another embodiment, an externally opening plunger port, aligned with the dispensing pathway, permits a simple, rod-like plunger or probe to be manually inserted into the applicator by the operator and pressed down the dispensing pathway to clear it, then removed from the applicator. Such a plunger could be disposable, a less costly and more convenient expedient than employing a disposable cannula. In a further alternative embodiment, the plunger can be removable and can be treated between uses, to remove adhering sealant and to sterilize the plunger, for example by immersion in a hot or boiling aqueous medium or by other known sterilizing means.

The applicator and dispensing method described in these aspects of the invention enhance the reusability of the applicator because the clearing member moving in the dispensing pathway can positively engage with, and dislodge clots of residual materials that could clog the applicator. Relatively high forces may be applied to clear clots. The ability quickly and easily to clear the actuator by operation of the clearing member is of particular value with fast-setting sealants, for example fibrin sealants used in surgical applications such as wound closure.

In a further aspect, the invention provides a manually operable sealant applicator capable of dispensing a coagulable sealant, the applicator having:

a) a variable volume reservoir for the sealant, the sealant being dischargeable from the reservoir by manually effected volume reductions;

b) a dispensing pathway for dispensing the sealant, the dispensing pathway communicating with the reservoir to receive the sealant therefrom; and c) a manually actuatable clearing member to move undesired materials along the dispensing pathway;

wherein the clearing member comprises a piston movable in a cylinder to provide suction and is communicable with the dispensing pathway to apply the suction to the dispensing pathway to withdraw the undesired materials therefrom.

This aspect of the invention provides the advantages of suction clearing which can be applied in a retrograde manner to withdraw liquid, as well as solid materials, from the dispensing pathway in a direction opposite to the direction of dispensing.

Sealant applicators according to the invention, with the described clearing functionality are particularly suitable for portable applications, for example, for field or emergency use, as they provide for clot clearing and reusability while avoiding need for connecting the applicator to an external service such as a vacuum source.

BRIEF DESCRIPTION OF THE DRAWINGS

One or more embodiments of the invention and of making and using the invention, as well as the best mode contemplated of carrying out the invention, are described in detail below, by way of example, with reference to the accompanying drawings, in which:

FIG. 1 is a schematic sectional view of a portion of a sealant applicator according to the invention, shown in a first position, the applicator employing a plunger for clearing clots;

FIG. 2 is a view similar to FIG. 1 of a portion of the sealant applicator in a second position;

DESCRIPTION OF THE PREFERRED EMBODIMENTS

Figure 3:
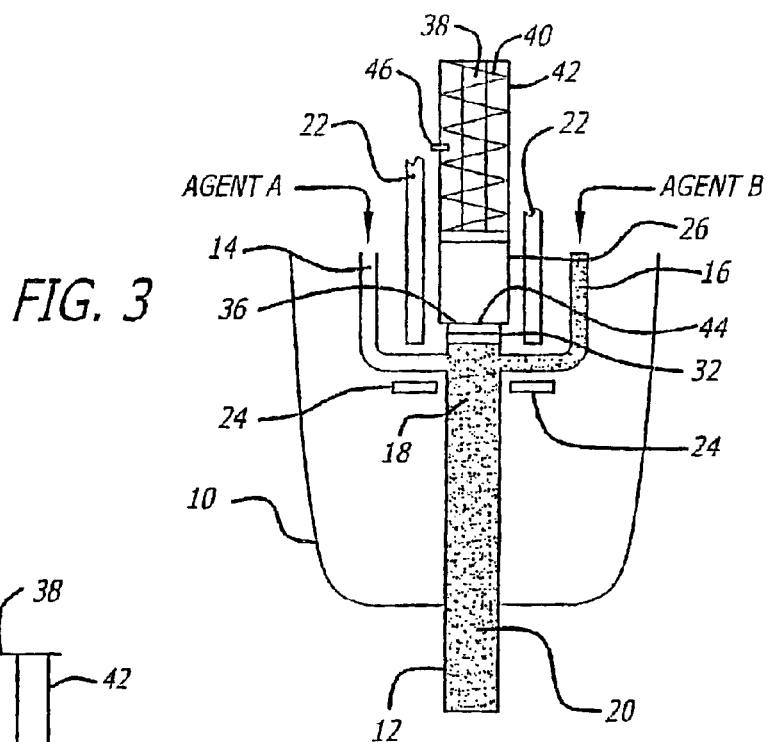
FIG. 3 is a view similar to FIG. 1 of another embodiment of applicator employing an air burst for clearing clots.

In one preferred embodiment of the invention the sealant applicator clearing member comprises an impeller to impel the undesired materials for removal from the dispensing pathway. The impeller can comprise an elongated member having a head portion insertable into, and forcibly movable along the dispensing pathway and an elongated portion extending externally of the dispensing pathway for effecting movement of the head portion along the dispensing pathway. Preferably, the impeller is movable along the dispensing pathway, in the direction of dispensing, by an applied mechanical, pneumatic or manual force.

The sealant applicator can comprise a mixing volume for mixing the at least two sealant agents in which case the clearing member may be actuatable or operable to remove undesired material from the mixing volume, for example by movement of the clearing member in the dispensing direction. One preferred clearing member comprises a plunger movable through the mixing volume, to clear the mixing volume, with the plunger traveling along the dispensing pathway in the dispensing direction. The plunger may have a cross-sectional configuration which is a close sliding fit within the dispensing pathway to dislodge and drive solids along the dispensing pathway in the dispensing direction.

The dispensing pathway can have a substantially constant cross-section throughout its length or may taper distally having a cross-sectional area which diminishes in the dispensing direction. In the latter case the plunger can comprise a head of variable dimension to be accommodated within the dispensing pathway's diminishing section. Other plunger configurations can be employed, as will be further described hereinbelow. If desired, the dispensing pathway can increase in cross-sectional area in the distal direction to aid in expulsion of undesired solid material from the dispensing pathway.

In some cases, the mixed sealant dispensing pathway may be substantially recti-linear and the plunger can be substantially rigid and have a straight configuration. In other cases, the mixed sealant dispensing pathway may be curved, or angled and the plunger can have a curved configuration to be accommodated in the dispensing pathway.

However, a particularly effective clearing action can be obtained with a clearing member that comprises a plunger movable through the dispensing volume wherein the plunger includes a distally extending portion for insertion into the dispensing pathway, is resiliently deformable and has a non-conforming configuration to engage the inner surface of the dispensing pathway. For example, where the dispensing pathway is straight, the plunger can be curved about an axis perpendicular to the direction of the dispensing pathway.

In an alternative embodiment, the clearing member comprises an impeller to apply a gas burst to the dispensing pathway to clear clots or debris from the dispensing pathway. The impeller can comprise a spring-loaded plunger movable in a cylinder to provide the gas burst.

In another embodiment, the applicator comprises a suction application pathway communicable with the dispensing pathway and the clearing member is operable to connect a source of gas pressure to the suction application pathway when communicating with the dispensing pathway, to apply the gas pressure to the dispensing pathway.

Preferably, the clearing member is mechanically coupled to the applicator to be supported by the applicator and is manually actuated by a resiliently biased control button. The clearing member can comprise a plunger having a head insertable into the dispensing pathway, and optionally the applicator can comprise a wiper to clean the head of the plunger when retracted.

In another embodiment the clearing member comprises a rod-like plunger and the applicator comprises a clearing port opening externally of the applicator and aligned with the dispensing pathway to permit the plunger to be manually inserted by a user into the dispensing pathway and to be moved along the dispensing pathway to clear the dispensing pathway.

Preferably, the dispensing pathway comprises a shuttle or clearing valve having a valve port movable between a closed dispensing position and an open clearing position wherein the dispensing pathway communicates with the clearing port through the valve port in the clearing position. The clearing valve and clearing member are interconnectable so that actuation of the clearing member moves the clearing valve into position to provide access to the dispensing pathway.

The applicator can comprise at least two reservoirs respectively for the at least two sealant agents, the reservoirs communicating one with each sealant agent supply pathway, and comprising a manually actuatable drive mechanism to drive the sealant agents from the reservoirs into the supply pathways. The applicator may be used for dispensing a fibrinogen sealant, in which case one of the at least two reservoirs may contain a fibrinogen agent and another of the at least two reservoirs may contain a thrombin agent or other fibrinogen activator. A manual dispensing actuator can be provided which actuator is operable to discharge sealant from the reservoir by reducing the reservoir volume. Preferably, the sealant applicator comprises a stop valve to stop flow of sealant from the reservoir to the dispensing pathway, said stop valve being operable when the clearing member is actuated.

The method of the invention can include manually operating a plunger to apply the impulsive force. Alternatively, the applied impulsive force can be a gas burst. In practicing the method of the invention, it will be understood that sealant dispensing should be terminated prior to activation of the impulse clearing plunger, and that residual sealant in the dispensing pathway will usually be dispelled from the applicator by the plunger.

Figures 1, 2:
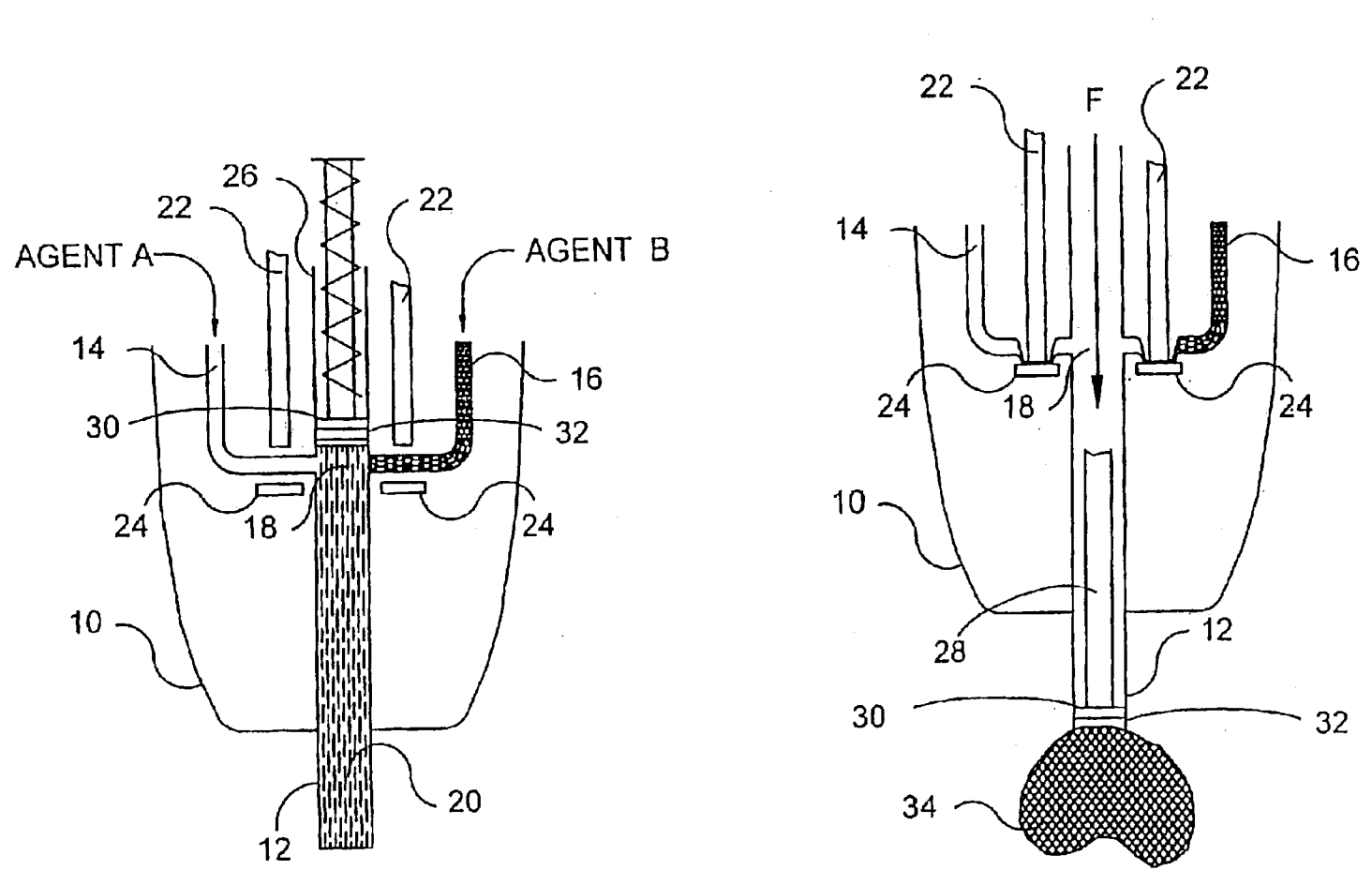

Referring now to the embodiment of the invention illustrated in FIGS. 1 and 2 of the drawings, the schematic views show how a tissue sealant applicator such as that disclosed in related application Ser. No. 09/037,160 can be modified to embody the present invention. The applicator depicted comprises an applicator tip 10 from which projects a dispensing cannula 12 into which open conduits 14 and 16 for sealant agents A and B respectively, at a mixing chamber 18. Sealant agents A and B can be supplied from reservoirs mounted on or in the applicator. When the applicator is actuated by a drive mechanism (not shown) sealant agents A and B are moved along conduits 14 and 16 respectively to be mixed in mixing chamber 18, forming a column 20 of mixed sealant in dispensing cannula 12.

To terminate flow of sealant agents A and B at the end of a cycle of sealant application, and to ready the device for a clearing cycle, a pair of pinch valves each comprising a clamp member 22 and a stop 24 is provided on either side of mixing chamber 18, to pinch and close agent conduits 14 and 16. For this purpose, conduits 14 and 16 are resiliently flexible, at least in the vicinity of clamp members 22.

Upwardly, with reference to the orientation shown in FIGS. 1 and 2, mixing chamber 18 communicates with a clearing conduit 26. Clearing conduit 26 is analogous to the suction clearing conduit shown in the related applications, but in the present invention instead of communicating with a suction control valve, clearing conduit is equipped with, or accessed by a clearing member, in this case, an movable plunger 28. Plunger 28 has a head 30 bearing seals 32 intended to wipe the interior of dispensing cannula 12 to remove undesired deposits and residuals therefrom. As shown, plunger 28 is elongated to permit plunger head 30 to be manipulated or otherwise moved, manually or by a manually controlled mechanical agent or other means external to mixing chamber 18 and cannula 12, as will be described. Preferably, cannula 12, mixing chamber 18 and clearing conduit 26 have similar cross-sectional shapes and areas such that plunger head 26 is a close sliding fit within all three members. Optionally, suction conduits and control valve structure similar to that disclosed in the related applications, that connect to an external vacuum source, may be provided to apply suction to prepare a work surface. However, the present invention does not employ an external suction source to clear cannula 12, as is disclosed in the related applications.

If desired, clearing conduit 26, the equivalent of which is connectable with the external vacuum source in embodiments of the inventions disclosed in the related applications, can be connected to a compressed air, or other compressed gas, source (not shown) to drive plunger 28 downwardly. Also, an optional tension spring 29 (FIG. 1 only) can be provided, to bias plunger 28 to return to an upward position, if desired.

As shown in FIG. 2, plunger 28 can be moved downwardly in response to an impulsive force F generated by a mechanical linkage, by air (or gas) pressure, by manual exertion or by other suitable means. Impulsive force F advances plunger 28 forwardly, or distally, to dispel column 20 of mixed sealant from cannula 12, discharging an effluent mass 34 externally of cannula 12 and clearing it. In its downward motion plunger 28 passes through mixing chamber 18 clearing that as well. The interior structural surfaces contacted by column 20 of mixed sealant are preferably formed of very smooth or highly polished material such as polished polypropylene or polytetrafluoroethylene, which resists bonding with the sealant mixture. Other suitable materials, surface finishes or coatings which resist bonding, for example silicones, will be apparent to those skilled in the art, and may, if desired, be selected according to the sealant employed in the applicator.

Impulse force F can be repeatedly applied, optionally with greater magnitude, if necessary, to dislodge stubborn clots.

As plunger 28 moves downwardly, clamp members 22, which are preferably mechanically coupled with plunger 28 for the purpose, pinch conduits 14 and 16 against stops 24 to terminate the flow of sealant agents A and B to mixing chamber 18.

The embodiment of FIG. 3, illustrates one possible way of achieving air-impulse clearing of clots. Referring to FIG. 3, cannula 12 is closed proximally, just above mixing chamber 18, by a slide valve 36. Slide valve 36 moves in tandem with clamp members 22 and is configured with a port (not shown), for example as disclosed in the above-referenced related applications, which can be brought into and out of registration with mixing chamber 18. While sealant is dispensed, clamp members 22 are disengaged and slide valve 36 closes the upper side of mixing chamber 18. When sealant dispensing ceases and clots, or possible clots, or other materials are to be removed from cannula 12, slide valve 36 moves with clamp members 22 so that when conduits 14 and 16 are pinched closed (FIG. 2), the port in slide valve 36 registers with mixing chamber 18, which communicates upwardly through the slide valve port with clearing conduit 26.

Above mixing chamber 18, a plunger 38 urged downwardly by a compression spring 40, is located in a cylinder 42 which communicates through a port 44 with mixing chamber 18 when slide valve 36 is in the open position. Plunger 38 can be retained in an upward, spring-loaded position by a releasable latch 46. Withdrawal of latch 46 from cylinder 42 releases plunger 38 which is driven rapidly downwardly in cylinder 42 discharging a burst of air through port 44 into mixing chamber 18 to clear the dispensing pathway. By employing a larger diameter for cylinder 42 than the diameter of cannula 12, amplification of the applied air pressure in cannula 12 can be achieved.

A compressed air source (not shown) can be connected to port 44 in place of plunger 38 and cylinder 42 to provide one or more clearing bursts of air, or controlled application of increasing pressure to remove stubborn clots. Such an air pressure source can be connected to the suction supply port and suction pathways of an applicator such as is disclosed in the above-referenced related applications, in place of a vacuum source, reversing the described air flow, so that the suction control valve can be used, in what is described as retrograde clearing mode, to apply selected or variable pressure to discharge clots and debris forwardly. Alternatively, a compressed gas source can be used, for example nitrogen or carbon dioxide, and may comprise a small cylinder stored on board the applicator, if desired, or a connection to an external source.

Figure 4:
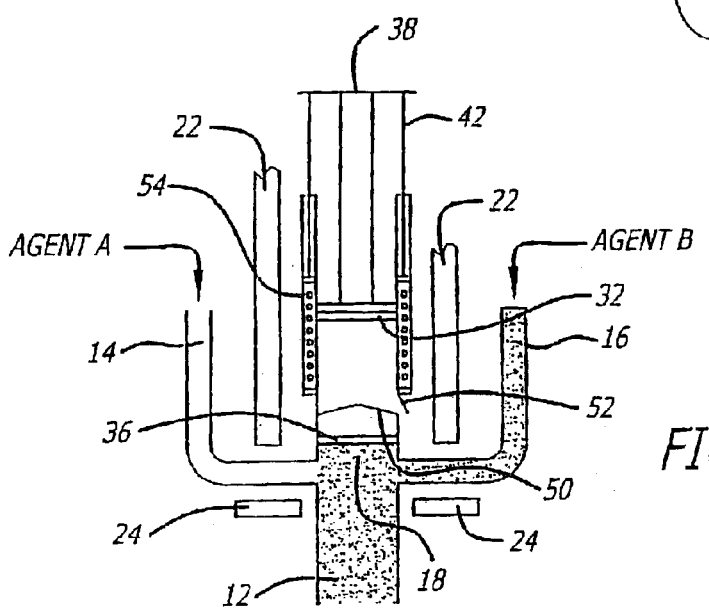
FIG. 4 is an enlarged, partial view, similar to FIG. 1, of a further embodiment of applicator employing manually generated suction for clearing clots.

Referring now to FIG. 4, the further embodiment of the invention illustrated comprises a modification of the invention shown in FIGS. 3 wherein, as an alternative to a gas burst, the force applied to clear cannula 12 of clots, residual sealant or other undesired material, comprises suction and the clearing member comprises a movable component of a manually operated suction pump. The suction pump is provided by appropriately modifying plunger 38 and cylinder 42. Thus, cylinder 42, which may optionally have a larger cross-section than that of cannula 12, to amplify the suctional force applied to cannula 12, is provided at its downward end with a flap-type one-way valve 50 controlling communication between cannula 12 and cylinder 42. One-way valve 50 operates to permit upward flow of materials into cylinder 42 and to close on a downward stroke preventing cylinder 42 from discharging into cannula 12. An air-release valve 52 permits air to be discharged from cylinder 42 on a downward stroke of plunger 38. Seal 32 is designed to provide a substantially air-tight seal with cylinder 42 sufficient to permit development of a negative pressure in cylinder 42 as plunger 38 is moved upwardly.

Optionally, plunger 38 is biased by a compression spring 54 disposed around cylinder 42 which can act on a sleeve 56 extending around plunger rod 43 to return plunger 38 to its uppermost position. If return spring 54 is employed to bias plunger 38 upwardly, a latch (not shown) can be provided to retain plunger 38 in a downward position with spring 54 loaded. Employment of slide valve 36 is also optional in this embodiment of the invention.

In use, while sealant is being applied, plunger 38 may be in either an upward or downward position, although the downward position is preferred. When sealant application terminates, clamp members 22 pinch conduits 14 and 16 against stops 24 to prevent further flow of sealant agents into cannula 12, readying the applicator for clearing.

Clearing is effected by moving plunger 38 upwardly, causing air-release valve 52 to close and one-way valve 50 to open, reducing the pressure in cylinder 42 and drawing the contents of cannula 12 upwardly. Plunger 38's movement can be effected by manually grasping the upper end of plunger 38, by releasing the latch holding return spring 54 in a compressed state or by a lever or other drive mechanism (not shown). If necessary, plunger 38 may be operated repeatedly to apply suction to cannula 12. Materials drawn into cylinder 42 can either be discharged through air-release valve 52, or tipped out of cylinder 42 by removing plunger 38 and inverting the applicator. Alternatively, the materials can simply be left in cylinder 42 and for disposal with the applicator.

Removability of plunger 38 permits a combination clearing method whereby a manually grasped probe or plunger is used to push material downwardly through cannula 12, with plunger 38 removed, plunger 38 is re-inserted and used to draw residuals out of cannula 12. Single-stroke clearing can permit coupling of movement of plunger 38 with the closing action of clamp members 22 enabling the functions to be effected by a single manual control, such as a push-button, dial or slide. However, if repeated operation of plunger 38 is desired during the clearing cycle, it is preferred that plunger 38 operate separately from clamping members 22 to avoid leakage of sealant agents into cannula 12 between strokes of plunger 38.

And while the invention has been described with reference to embodiments adapted for mixing and dispensing a sealant comprising a mixture of two sealant agents A and B, it will be understood that the invention can also be beneficially embodied in applicators for one-component sealants, adhesives or glues to permit clearing of dispensing tips or cannulas subject to clogging. In such case, a single sealant reservoir or conduit 14 or 16 will be employed. Provision of a port, such as port 44, opening into a dispensing conduit upstream from a dispensing tip or aperture and closable by plunger 28, plunger 38 or slide valve 36, provides access to the dispensing tip or cannula for clearing with a plunger, gas burst or the like, while use of a pinch valve or other suitable valve to stop the flow of sealant, or sealant agent, from a conduit such as 14 or 16 avoids contamination of the tip with fresh sealant during the clearing process.

It will be understood that a mechanically or pneumatically driven clearing process, may be manually actuated and also manually augmented, for example, by manual removal of any plug or "worm" of coagulated sealant that projects externally from cannula 12. Also, clearing should preferably be effected immediately after sealant application, before liquid sealant within cannula 12 sets up. These steps can be followed to provide a,clean applicator for the next cycle of sealant application, even where substantial time elapses between applications.

Figure 5:
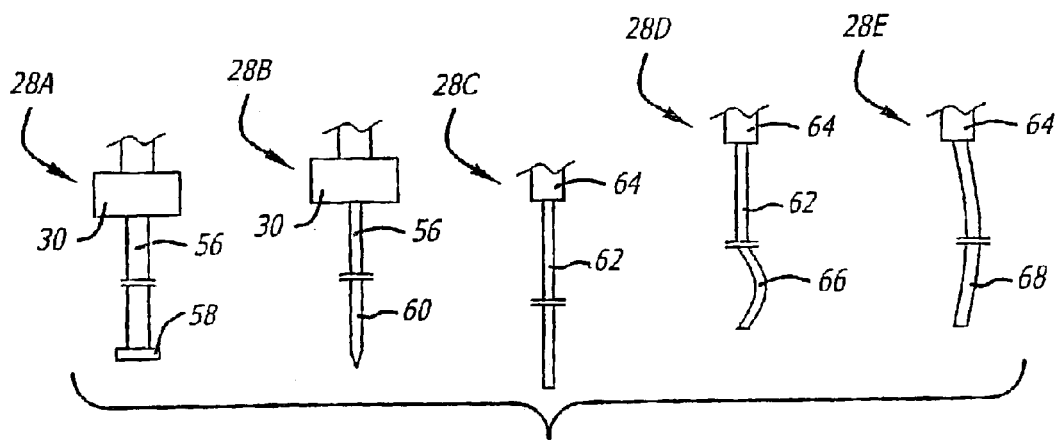
FIG. 5 illustrates in side elevational view a number of different modified plungers for use in a sealant applicator such as shown in FIGS. 1–2.

FIG. 5 shows several possible designs of plunger 28, variously labeled 28A–28E, that may be used to apply an impulse clearing force in a sealant applicator such as that shown in FIGS. 1 and 2. These various designs will suggest to those skilled in the art other possible designs or configurations of plunger 28 that may be used, for example, coiled, sinuous and the like. Plungers 28A and 28B retain plunger head 30 to clean the mixing chamber at the top of cannula 12 and employ a proboscis or probe 56 that extends distally from plunger head 30 to facilitate clearing of cannula 12. The length of probe 56 is selected according to the extent of entry into cannula 12 that is required.

In the case of plunger 28A, probe 56 terminates in a small disk 58 of lesser diameter than plunger head 30, which can be inserted into tapering distal portions of cannula 12, to clean them.

In the case of plunger 28B, probe 56 terminates in a point 60 which, if probe 56 is sufficiently long in relation to cannula 12, to be inserted through cannula 12's dispensing aperture, pushing out the clot or other residuals.

Other configurations of probe 56 will be apparent to those skilled in the art. For example, probe 56 could have a complementary shape to fit closely within cannula 12, for example, a tapering shape, or disk 58, or an equivalent end piece, could be similar in size to plunger head 30 and be resiliently deformable to conform to a tapering cannula.

While in some cases it may be desirable for plunger 28 to have a configuration which conforms with the configuration of the dispensing pathway provided by mixing chamber 18 and cannula 12, in other cases an improved clearing action may be obtained by employing a plunger configuration which does not conform with the dispensing pathway, but forcibly engages the inner surface thereof. Plungers 28 C–E have such configurations when employed for clearing a dispensing pathway which is not rectilinear.

Plunger 28C, lacks plunger head 30 and comprises a straight rod 62 depending from a base member 64. Base member 64 serves to connect plunger 28C to a mechanical or pneumatic drive, as described hereinabove or, alternatively, can be manipulated by hand. Preferably, rod 62 has sufficient resilient flexibility to be insertable into a curved or angled dispensing pathway, should such be the configuration provided by mixing chamber 18 and cannula 12, where rod 62 can forcibly engage the inside surfaces subject to contamination with coagulated sealant.

Plunger 28D is similar to plunger 28C except that its lower portion 66 is curved about an axis perpendicular to the extent of rod 62.

Plunger 28E is similar to plunger 28D except that rod 68 is curved throughout its length. Plungers 28D and 28E can be inserted into a substantially straight or rectilinear dispensing pathway and will conform resiliently to the inner surface of the dispensing pathway, exerting a substantially clearing force to dislodge undesired materials therefrom with suitable manual or mechanical manipulations of the plunger.

If desired, the clearing action of plunger 28 or its variants 28A–28E, can comprise a rotational or vibrational or reciprocatory movement, or combinations of such movements, to enhance the clearing action.

Preferably, such probe-like extended plungers 28A–E, if employed, are retracted from cannula 12 while sealant is being dispensed. It will also be understood that such plungers or probes can be manually grasped and manipulated or mechanically or pneumatically driven in response to mechanical actuation, and could be disposable, if desired. Optionally, for the case of a manually manipulated clearing plunger, a sealant applicator having a housing can be provided with a suitably disposed opening in the housing to permit the plunger to be manipulated externally of the housing.

In another embodiment (not shown), the novel applicators described herein can be adapted to dispense mixed tissue sealant as a spray, if desired, by employing the gas-entrainment invention disclosed in related Epstein U.S. patent application Ser. No. 09/302,726 filed Apr. 30, 1998.

While illustrative embodiments of the invention have been described above, it is, of course, understood that various modifications will be apparent to those of ordinary skill in the art. Many such modifications are contemplated as being within the spirit and scope of the invention.

What is claimed is:
1. A manually operable sealant applicator, comprising:
 a) at least two supply pathways for respectfully supplying at least two sealant agents;
 b) a dispensing pathway for dispensing a mixture of the at least two sealant agents, the dispensing pathway communicating with the at least two supply pathways; and c) a manually actuable clearing member to move undesired materials along the dispensing pathway, the clearing member comprising an impeller having an elongated member, a head portion insertable into, and forcibly movable along the dispensing pathway, and an elongated portion extending externally of the dispensing pathway for effecting movement of the head portion along the dispensing pathway.

2. A manually operable sealant applicator, comprising:
a) at least two supply pathways for respectfully supplying at least two sealant agents;
b) a dispensing pathway for dispensing a mixture of the at least two sealant agents, the dispensing pathway communicating with the at least two supply pathways; and
c) a manually actuable clearing member to move undesired materials along the dispensing pathway, the clearing member comprising a plunger movable through a mixing volume and configured to clear the mixing volume, the plunger traveling along the dispensing pathway in the dispensing direction.

3. The applicator according to claim 2 wherein the plunger is configured to slide within the dispensing pathway to dislodge and drive solids along the dispensing pathway in the dispensing direction.

4. The applicator according to claim 3 wherein the dispensing pathway has a substantially constant cross-section throughout the length of the dispensing pathway.

5. The applicator according to claim 2 wherein the dispensing pathway tapers distally and having a cross-sectional area which diminishes in a dispensing direction, the plunger comprising a head of variable dimension to be accommodated within the dispensing pathway.

6. The applicator according to claim 2 wherein the dispensing pathway increases in cross-sectional area in the distal direction to aid in expulsion of undesired solid material from the dispensing pathway.

7. The applicator according to claim 2 wherein the dispensing pathway is substantially recti-linear and the plunger is substantially rigid and has a straight configuration.

8. The applicator according to claim 2 wherein the dispensing pathway is curved and the plunger has a curved configuration to be accommodated within the dispensing pathway.

9. A manually operable seal applicator, comprising:
a) at least two supply pathways for respectfully supplying at least two sealant agents;
b) a dispensing pathway for dispensing a mixture of the at least two sealant agents, the dispensing pathway communicating with the at least two supply pathways; and
c) a manually actuable clearing member to move undesired materials along the dispensing pathway, the clearing member comprising a plunger movable through the dispensing pathway wherein the plunger includes a distally extending portion insertable into the dispensing pathway, the plunger configured to be resiliently deformable and having a non-conforming configuration to engage the inner surface of the dispensing pathway.

10. The applicator according to claim 9 wherein the dispensing pathway is straight and the plunger is curved about an axis perpendicular to the direction of the dispensing pathway.

11. A manually operable sealant applicator, comprising:
a) at least two supply pathways for respectively supplying at least two sealant agents;
b) a dispensing pathway for dispensing a mixture of the at least two sealant agents, the dispensing pathway communicating with the at least two supply pathways; and
c) a manually actuable clearing member to move undesired materials along the dispensing pathway, the clearing member comprising a plunger having a head, the applicator comprising a wiper to clean the head of the plunger when retracting.

12. A manually operable sealant applicator, comprising:
a) at least two supply pathways for respectfully supplying at least two sealant agents;
b) a dispensing pathway for dispensing a mixture of the at least two sealant agents, dispensing pathway communicating with the at least two supply pathways; and
c) a manually actuable clearing member to move undesired materials along the dispensing pathway, the clearing member comprising a rod-like plunger, the applicator having a clearing port opening externally and aligned with the dispensing pathway to permit the plunger to be manually inserted into the dispensing pathway.

13. The sealant applicator according to claim 12 wherein the dispensing pathway comprises a valve movable between a close dispensing position and an open clearing position wherein the dispensing pathway communicates with the clearing port through the valve port in the clearing position.

14. A manually operable sealant applicator, comprising:
a) a variable volume reservoir for a sealant, the sealant being dischargeable from a sealant reservoir by manually effected volume reductions;
b) a dispensing pathway for dispensing the sealant, the dispensing pathway communicating with the sealant reservoir to receive the sealant therefrom;
c) a clearing valve communicating with the dispensing pathway and being movable between the dispensing position and a clearing position, the clearing valve providing access to the dispensing pathway in the clearing position; and
d) a manually actuable clearing member operable through the access provided by the clearing valve to move undesired materials along the dispensing pathway, the clearing member comprising a reciprocatable plunger configured to dislodge undesired materials therein and retractable to permit sealant dispensing.

* * * * *